United States Patent
Rodriguez

(10) Patent No.: US 6,508,430 B1
(45) Date of Patent: Jan. 21, 2003

(54) SELF-APPLICATOR FOR BANDAGES

(76) Inventor: Jose Luis Corrales Rodriguez, Urb. La Ribera, 39 Casa Concordia, 18690 Almuñecar, Granada (ES)

( * ) Notice: Subject to any disclaimer, the term of this patent is extended or adjusted under 35 U.S.C. 154(b) by 0 days.

(21) Appl. No.: 09/690,467

(22) Filed: Oct. 18, 2000

(30) Foreign Application Priority Data

Oct. 18, 1999 (ES) ............................................. 9902607

(51) Int. Cl.⁷ ............................................. B65H 18/14
(52) U.S. Cl. .............................. 242/546.1; 242/588.2; 242/597.6
(58) Field of Search ........................... 242/546.1, 588.2, 242/422.4, 396.8, 405.2, 597.6

(56) References Cited

U.S. PATENT DOCUMENTS

| | | | | |
|---|---|---|---|---|
| 4,248,392 A | * | 2/1981 | Parry | 242/422.1 |
| 4,484,717 A | * | 11/1984 | Goldstein | 242/422.1 |
| 4,714,211 A | * | 12/1987 | Hwang | 242/423.1 |
| 4,722,493 A | * | 2/1988 | Parry | 242/422.4 |
| 4,784,348 A | * | 11/1988 | McDonald | 242/422.4 |
| 4,817,762 A | * | 4/1989 | Powell | 188/67 |
| 4,834,312 A | * | 5/1989 | Riemenschneider, III | 242/588.2 |
| 4,872,623 A | * | 10/1989 | Parry | 242/422.4 |
| 5,203,517 A | * | 4/1993 | Parry | 242/422.4 |
| 5,351,905 A | * | 10/1994 | Ferber | 242/588.2 |
| 5,524,843 A | * | 6/1996 | McCauley | 242/532.6 |
| 5,664,739 A | * | 9/1997 | Black | 242/588.2 |
| 5,927,635 A | * | 7/1999 | Black | 242/395 |
| 6,102,323 A | * | 8/2000 | Riemenschneider | 242/422.4 |
| 6,286,779 B1 | * | 9/2001 | Devine | 242/532 |

FOREIGN PATENT DOCUMENTS

| | | | |
|---|---|---|---|
| GB | 2203726 A | * | 10/1988 |
| GB | 2299321 A | * | 10/1996 |
| GB | 2333506 A | * | 7/1999 |

* cited by examiner

Primary Examiner—William A. Rivera
(74) Attorney, Agent, or Firm—Law Offices of David G. Posz; Kerry S. Culpepper

(57) ABSTRACT

A self-applicator for bandages includes a tubular body with two widened areas. One widened area has a greater length than the other widened area. At the one widened area, two internal and opposite semi-bushings are dovetailed to form a handle. At the other end of the tubular body, internal ribs provided in an axial direction are coupled to end ribs of a tubular part over which a bandage is wound. The bandage tension is adjusted at any time by pressing a finger over the other widened area of the tubular body.

5 Claims, 2 Drawing Sheets

SELF-APPLICATOR FOR BANDAGES

This application claims the priority of Spanish patent document 99023607, filed Oct. 18, 1999, the disclosure of which is expressly incorporated by reference herein.

FIELD OF THE INVENTION

The present invention is directed to a self-applicator for bandages that modifies the concept and the way in which a bandage is applied to any area of a person's body.

BACKGROUND AND SUMMARY OF THE INVENTION

The traditional method of applying a bandage requires the use of both hands of the person applying it over an area to be protected.

On the other hand, it is necessary to unroll the bandage with the fingers while the package is moved around said area.

Therefore, it is extremely difficult for people with mobility handicaps in their fingers to rapidly apply a bandage on such an area.

Another disadvantage of bandage application is that of obtaining a uniform tension which depends on the changing of hands necessary for correct application which is always a slow and difficult process.

By using the self-applicator for bandages of the present invention, the aforementioned disadvantages and difficulties are avoided, since a rapid application is achieved. In addition, tension control of the bandage, hand contact with the bandage, and even more importantly, finger mobility, are almost nil.

According to the present invention, the self-applicator comprises a tubular body having two widened areas.

One widening has a greater diameter than the other widening and is located at one end of the tubular body. This widening has internal recesses in an axial direction. The internal recesses are coupled with a tubular part via external ribs on the tubular part. The end of a bandage is rolled around the tubular part and fixed.

In a first widened area having a greater length than the second widening of the tubular body, two semi-bushings are dovetailed to form the applicator handle.

The second widened area with a greater diameter has small linear salients in its surface parallel to a ruling line, thereby permitting the application of a small pressure with the finger to slow down rotation of a bandage and the tubular body, and hence give more or less tension during bandage application.

Other objects, advantages and novel features of the present invention will become apparent from the following detailed description of the invention when considered in conjunction with the accompanying drawings.

DETAILED DESCRIPTION OF THE DRAWINGS

Figure 1:
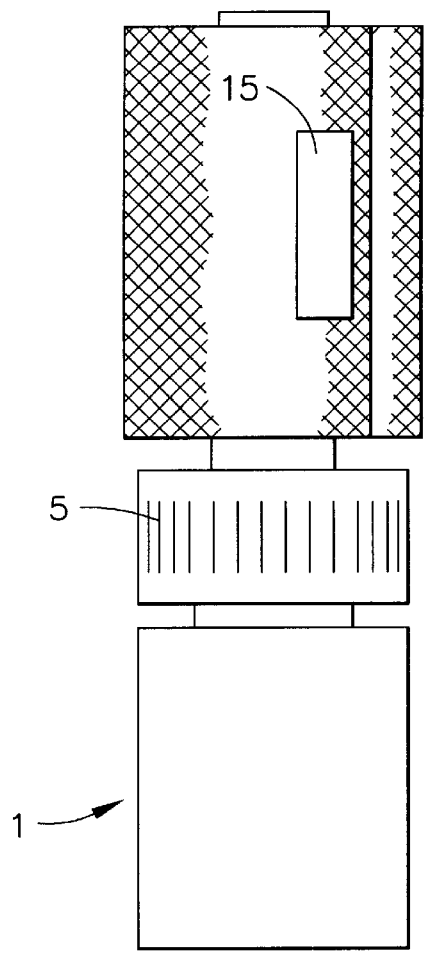
FIG. 1 shows a side view of the self-applicator of the present invention.
Figure 2:
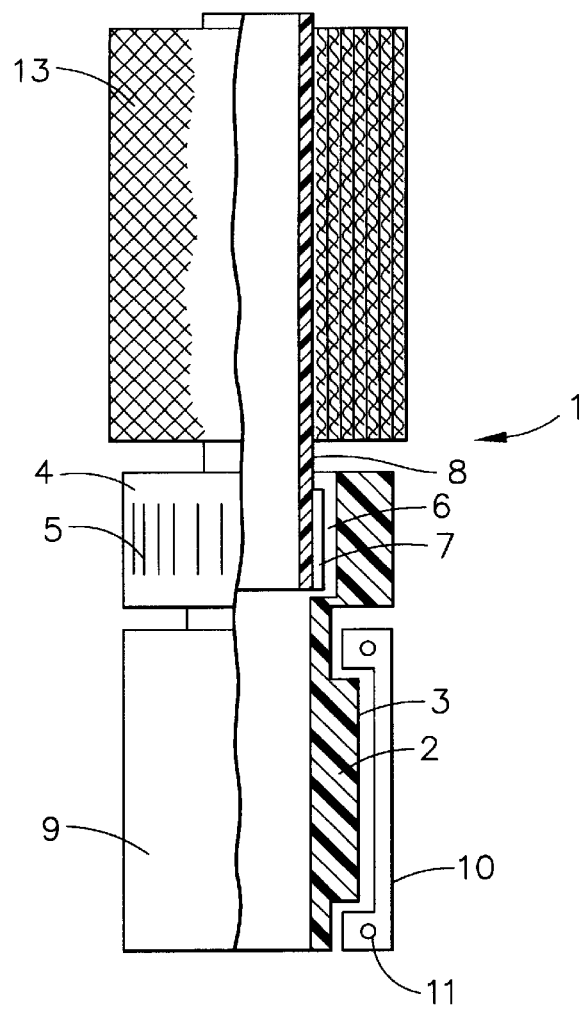
FIG. 2 shows a sectioned view of FIG. 1.
Figure 3:
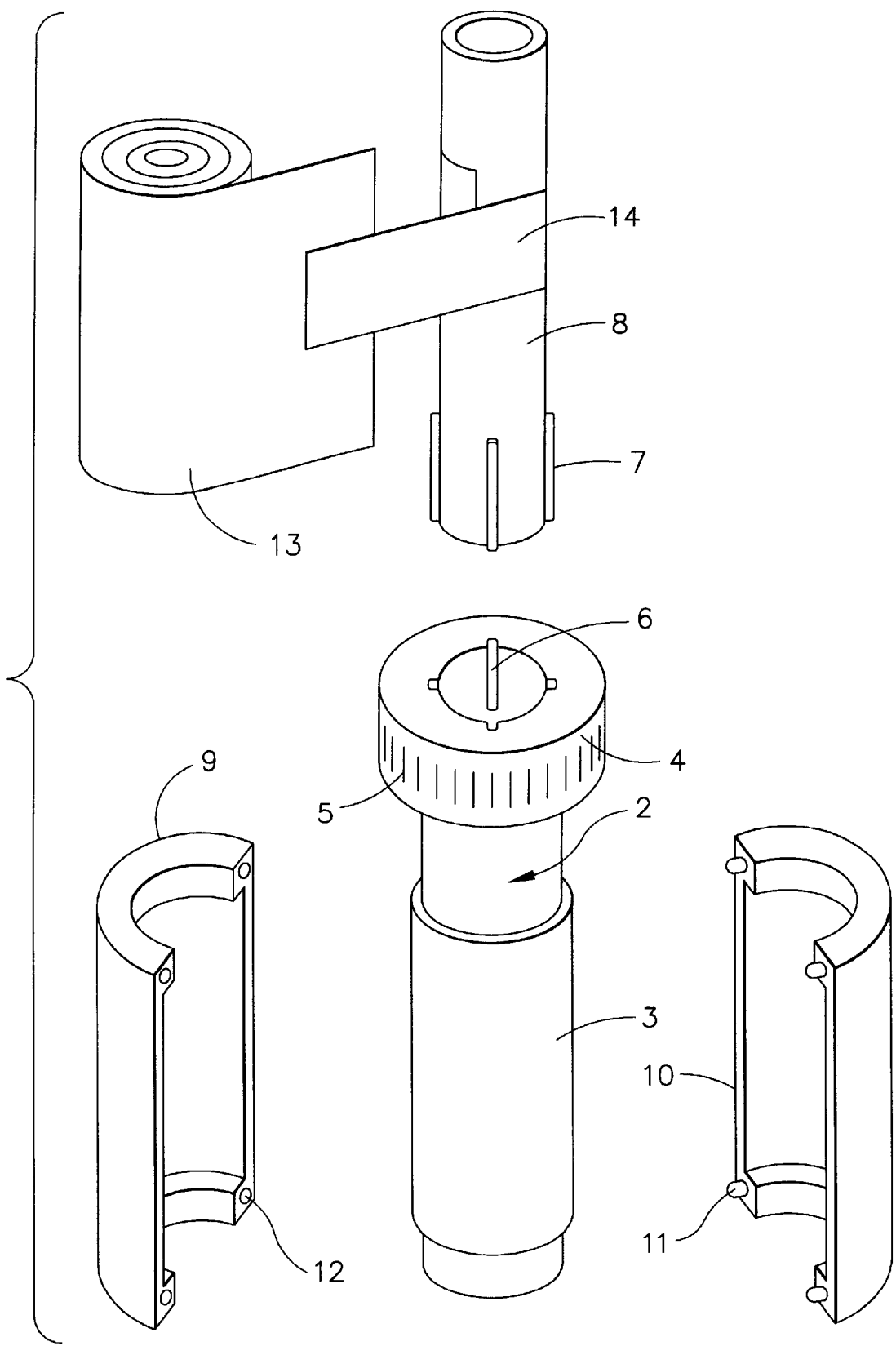
FIG. 3 shows a breakdown of FIG. 1.

The self-applicator 1 comprises a tubular body 2 having a widening 3 of greater length than a widening 4 at the other end. Widening 4 has a greater diameter than widening 3 and has linear salients 5 in a ruling line direction.

The free end of widening 4 has recesses 6 that are coupled with ribs 7 forming tubular part 8.

At widening 3 and through the end of tubular body 2, two equal and opposite semi-bushings 9 and 10 are coupled, which are fixed by dovetailing on coupling protuberances 11 in opposite housings 12.

Once coupled, semi-bushings 9 and 10 form the corresponding handle of the applicator.

At the tubular part 8, bandage 13 is wound by (1) an adhesive component 14, thereby permitting the bandage to be centered; and (2) another adhesive component 15, thereby allowing the bandaging operation to be started.

When bandaging is started, the applicator is rotated with the handle. When it is desired to provide greater tension to the bandage, the applicator is slowed down by placing a finger on the end 4. In this way, the tension that should be given to the bandage is regulated, besides facilitating this operation with the appropriate use of the applicator.

Having sufficiently described the invention, and the practical use thereof, it should be mentioned that the aforementioned arrangements, represented in the attached drawings may be modified in detail, as long as the basic principle is not changed.

What is claimed is:

1. A self-applicator for bandages, comprising:
   a tubular body having two widened areas, a first widened area having a greater length than a second widened area, said second widened area having internal recesses in an axial direction;
   two dovetailed semi-bushings surrounding said first widened area, thereby forming an applicator handle; and
   a tubular part over which a bandage is wound and having external ribs coupled to said internal recesses of said second widened area.

2. A self-applicator for bandages according to claim 1, wherein said second widened area has linear projections.

3. A method of applying a bandage using the self-applicator according to claim 1, comprising;
   winding a bandage over said tubular part via a first adhesive component;
   attaching the bandage to said tubular part via a second adhesive component; and
   adjusting the tension of said bandage by pressing a finger over said second winding area.

4. A self applicator for bandages according to claim 1, wherein said second widened area has linear projections and said second widened area communicates torque to said tubular part via said internal recesses that are coupled to said external ribs of said tubular part.

5. A self applicator for applying a bandage comprising:
   a tubular member that includes a tubular part for defining an axis of rotation and a tubular body for defining a stable base, wherein said tubular part includes a plurality of exterior ribs and said tubular body includes a first widened area and a second widened areas;
   said first widened area having a length greater than said second widened area for defining a handle region and said second widened area having a diameter greater than said first widened area for defining a brake-by-tension region;
   first and second semi-bushings coupled together over said handle region for defining a handle; and
   a series of linear projections on said second widened area for defining a brake-by-tension region and a plurality of interior recesses for receiving said exterior ribs of said tubular part.

* * * * *